(12) United States Patent
Chandrasekhar et al.

(10) Patent No.: US 11,932,654 B2
(45) Date of Patent: Mar. 19, 2024

(54) NIMBOLIDE ANALOGS AS ANTI-CANCER AGENTS AND PREPARATION THEREOF

(71) Applicant: Council of Scientific & Industrial Research, New Delhi (IN)

(72) Inventors: Srivari Chandrasekhar, Hyderabad (IN); Prathama Satyendra Mainkar, Hyderabad (IN); Karre Nagaraju, Hyderabad (IN); Togapur Pavan Kumar, Hyderabad (IN); Ummanni Ramesh, Hyderabad (IN); Kanchanapally Tejaswini, Hyderabad (IN); Jerald Mahesh Kumar, Hyderabad (IN); Katragadda Suresh Babu, Hyderabad (IN); Boggavarapu Subrahmanya Sastry, Hyderabad (IN); Debabrata Mukhopadhyay, Hyderabad (IN)

(73) Assignee: Council of Scientific & Industrial Research (IN)

( * ) Notice: Subject to any disclaimer, the term of this patent is extended or adjusted under 35 U.S.C. 154(b) by 141 days.

(21) Appl. No.: 17/171,276

(22) Filed: Feb. 9, 2021

(65) Prior Publication Data
US 2021/0171538 A1 Jun. 10, 2021

Related U.S. Application Data

(62) Division of application No. 16/172,045, filed on Oct. 26, 2018, now Pat. No. 10,947,249.

(30) Foreign Application Priority Data

Jan. 5, 2018 (IN) .............................. 201811000561

(51) Int. Cl.
    *C07D 493/06*     (2006.01)
    *A61P 35/00*     (2006.01)
    *C07D 493/04*     (2006.01)

(52) U.S. Cl.
    CPC ............ *C07D 493/04* (2013.01); *A61P 35/00* (2018.01)

(58) Field of Classification Search
    CPC .................................................. C07D 493/06
    See application file for complete search history.

(56) References Cited

U.S. PATENT DOCUMENTS 10,947,249 B2 * 3/2021 Chandrasekhar .... C07D 493/04

FOREIGN PATENT DOCUMENTS

WO     2015035199 A1     3/2015
WO     WO-2015035199 A1 *     3/2015 ........... A61K 31/343

OTHER PUBLICATIONS

Biswas, K., et al. "Biological activities and medicinal properties of neem (Azadirachta indica)." Current Science, (Jun. 10, 2002), vol. 82, No. 11, pp. 1336-1345 (Year: 2002).*
Cui, Baoliang, et al. "Limonoids from Azadirachta Excelsa." Phytochemistry. (1998), vol. 47, No. 7, pp. 1283-1287. (Year: 1998).*
Rojanapo W, Suwanno S, Somjaree R, Glinsukon T, Thebtaranont Y. Mutagenic and antibacterial activity testing of nimbolide and nimbic acid. J Sci Soc Thailand. Dec. 1, 1985;11(11):177-81.
Suresh G, Gopalakrishnan G, Wesley SD, Pradeep Singh ND, Malathi R, Rajan SS. Insect antifeedant activity of letranortriterpenoids from the Rutales. A perusal of structural relations. Journal of agricultural and food chemistry. Jul. 31, 2002;50(16):4484-90.
Biswas K, Chattopadhyay I, Banerjee RK, Bandyopadhyay U. Biological activities and medicinal properties of neem (Azadirachta indica). Current Science-Bangalore-. Jun. 10, 2002;82(11):1336-45.
Anitha G, Raj JJ, Krishnan VR, Narasimhan S, Solomon KA, Rajan SS. Semi-synthetic modification of nimbolide to 6-homodesacetylnimbin and 6-desacetylnimbin and their cytotoxic studies. Journal of Asian natural products research. Feb. 1, 2007;9(1):73-8.
Kigodi PG, Blaskó G, Thebtaranonth Y, Pezzuto JM, Cordell GA. Spectroscopic and biological investigation of himbolide and 28-deoxonimbolide from Azadirachta indica. Journal of natural products. Nov. 1989;52(6):1246-51.

(Continued)

*Primary Examiner* — John S Kenyon
(74) *Attorney, Agent, or Firm* — Lerner David LLP

(57) ABSTRACT

The present invention relates to nimbolide analogs useful as anti-cancer agents and preparation thereof. Particularly the present invention relates to nimbolide analogs of general formula I.

Formula I

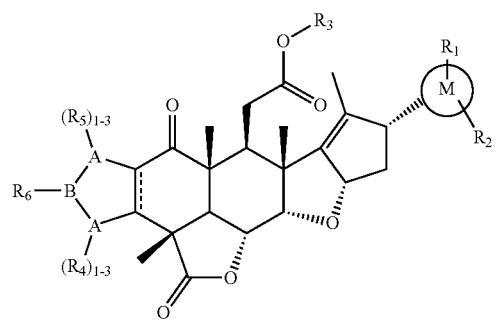

wherein, ring M is any ring selected from the group consisting of substituted or unsubstituted aryl, heteroaryl, cycloalkyl and heterocyclic; A and B are selected from the group consisting of C, O, N, S and H; $R_1$, $R_2$, $R_3$, $R_4$, $R_5$ and $R_6$ are selected from the group consisting of C1-C6 alkyl, aryl, heteroaryl, C1-C7 cycloalkyl, heteroalkyl, hydrogen, hydroxy, alkoxy, nitro, halogen, amino, alkylamino, aryl amino and cyano; wherein each of these groups may be further substituted with one or more substituents selected from the group consisting of hydrogen, hydroxy, halogen, cyano, alkyl amino, aryl amino, alkoxy, amino, nitro, aldehyde, carboxylic acid and ester.

9 Claims, 6 Drawing Sheets

(56) References Cited

OTHER PUBLICATIONS

Cohen E, Quistad GB, Casida JE. Cytotoxicity of nimbolide, epoxyazadiradione and other limonoids from neem insecticide. Life sciences. Feb. 23, 1996;58(13):1075-81.
World Cancer Report 2014, World Health Organization 2014, Bernard W. Stewart and Christopher P. Wild, editors; Chapter 1.1, pp. 16-53, published by The International Agency for Research on Cancer, ISBN 978-92-832-0443-5.

* cited by examiner

NIMBOLIDE ANALOGS AS ANTI-CANCER AGENTS AND PREPARATION THEREOF

This application is a divisional of U.S. application Ser. No. 16/172,045 filed on Oct. 26, 2018, which claims priority from Indian Patent Application No. 201811000561 filed on Jan. 5, 2018, the disclosures of which are incorporated herein by reference in their entirety.

FIELD OF THE INVENTION

The present invention relates to nimbolide analogs useful as anti-cancer agents and preparation thereof. Particularly the present invention relates to nimbolide analogs of general formula I

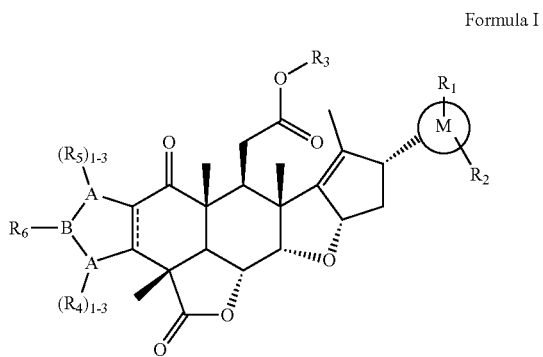

Formula I wherein, ring M is any ring selected from the group consisting of substituted or unsubstituted aryl, heteroaryl, cycloalkyl and heterocyclic;
A and B are selected from the group consisting of C, O, N, S and H;
$R_1$, $R_2$, $R_3$, $R_4$, $R_5$ and $R_6$ are selected from the group consisting of C1-C6 alkyl, aryl, heteroaryl, C1-C7 cycloalkyl, heteroalkyl, hydrogen, hydroxy, alkoxy, nitro, halogen, amino, alkylamino, aryl amino and cyano; wherein each of these groups may be further substituted with one or more substituents selected from the group consisting of hydrogen, hydroxy, halogen, cyano, alkyl amino, aryl amino, alkoxy, amino, nitro, aldehyde, carboxylic acid and ester.

BACKGROUND OF THE INVENTION

Cancer is the second leading cause of death worldwide. It caused about 8.2 million deaths or 14.6% of all human deaths. The risk of cancer increases significantly with age and many cancers occur more commonly in developed countries. Most of the cancer treatments rely heavily on chemotherapy, despite its limitations. Due to the lack of selectivity chemotherapeutic drugs can also kill normal cells. They might cause multidrug resistance (MDR) as well as result in serious side effects, immunity suppression, and poor treatment outcomes. Throughout the ages, nature is the best source of medicines for human diseases. Majority of drugs have been generated from natural products (secondary metabolites from plants, animals) and compounds derived from natural products. More than half of currently available drugs are natural compounds or are related to them, and in the case of cancer this proportion surpasses 60%. Natural products remain the best sources of drugs and drug leads.

Natural compound's structural modification has led to more potent and less toxic compounds than the prototype. In addition, the possibility of generating hybrids of natural products seems to be very promising in the development of new lead compounds with better activity than that of the parent compound. Neem tree (Azadiracta indica) is indigenous to Indian subcontinent. It is widely grown in Southeast Asia (India, Bangladesh, Pakistan, Burma and Nepal), West Africa and other tropical parts of the world. All parts of the neem tree offer tremendous potential for medicinal, agricultural and industrial exploitation and have been evaluated for antiinflammatory, antipyretic, antihistamine, antifungal, antitubercular, antiprotozoal, vasodilatory, antimalarial, diuretic, spermicidal, antiarthritic, antiprotozoal, insect repellent, antifeedant and antihormonal activities.

Several potentially bioactive compounds (over 300) were isolated from Azadirachta indica, among which limonoids (around 100) are the major group. Limonoids, are highly oxygenated, modified triterpenes formed as secondary metabolites by plants in the Meliaceae and Rutaceae families. Limonoids have attracted considerable research attention as promising candidates for cancer chemoprevention. Nimbolide was first isolated by Nigerian scientist D. E. U. Ekong from fresh neem leaves using petroleum spirit. Nimbolide can be isolated from leaves and seed extracts of Azadirachta indica and it has been shown to exhibit numerous biological activities such as anti-feedent anti-malarial, antimicrobial, and anti-cancer activity. Nimbolide in combination with cephalosporin antibiotics showed significant synergistic activity against wound infecting pathogens. Further nimbolide exhibited the most promising anticancer activity than other pharmacological activities. Previously, a number of analogs of nimbolide were synthesized and evaluated for various biological activities. These compounds were found to exhibit prominent anti-cancer activity. Therefore, there is a need for the development of new and diversely substituted nimbolide functional analogues and evaluation of their biological properties. The following are the references related to the invention. CA2224115A1; CN101972246; U.S. Pat. Nos. 5,370,873; 7,179,927; US20140242199; WO9417815; WO2007072500; WO2014141094; WO2015035199; World Cancer Report 2014, World Health Organization 2014. pp. chapter 1.1 ISBN 9283204298; Cancer Chemother Rep, 1968, 52, 455; Curr. Sci. 2002, 82, 1336; Agric. Food Chem. 2002, 50, 4484; Southeast Asian J. Trop. Med. Public Health 1985, 16, 66; J. Sci. Soc. Thailand 1985, 11, 177; J. Nat. Prod. 1989, 52, 1246; Life Sci. 1996, 1075; RSC Adv. 2011, 5, 1; Journal of Asian Natural Products Research, 9, 1, 2007, 73. In this context a library of nimbolide derivatives with diverse structural features have been synthesized and evaluated for their anticancer potential.

OBJECTIVE OF THE INVENTION

The main objective of the present invention is to provide new nimbolide analogs as useful anticancer agents.

Another objective of the present invention is to provide the process for the preparation of these new nimbolide derivatives.

SUMMARY OF THE INVENTION

The above and other objectives of the present invention are achieved by providing the new nimbolide analogs, which have been synthesized by diverse functional modifications on the basic nimbolide core. Accordingly, the present invention affords a new class of nimbolide analogs of general formula I Formula I

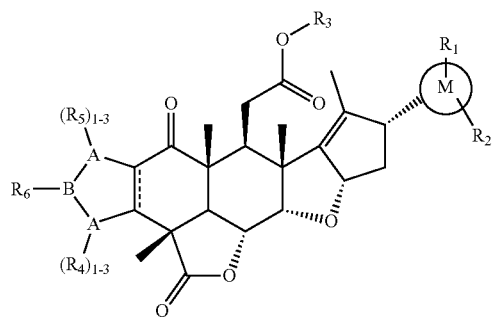

wherein, ring M is any ring selected from the group consisting of substituted or unsubstituted aryl, heteroaryl, cycloalkyl and heterocyclic;

A and B are selected from the group consisting of C, O, N, S and H;

$R_1$, $R_2$, $R_3$, $R_4$, $R_5$ and $R_6$ are selected from the group consisting of C1-C6 alkyl, aryl, heteroaryl, C1-C7 cycloalkyl, heteroalkyl, hydrogen, hydroxy, alkoxy, nitro, halogen, amino, alkylamino, aryl amino and cyano; wherein each of these groups may be further substituted with one or more substituents selected from the group consisting of hydrogen, hydroxy, halogen, cyano, alkyl amino, aryl amino, alkoxy, amino, nitro, aldehyde, carboxylic acid and ester.

In a preferred embodiment, nimbolide analogs are selected from the group consisting of (A2 to A10)

2

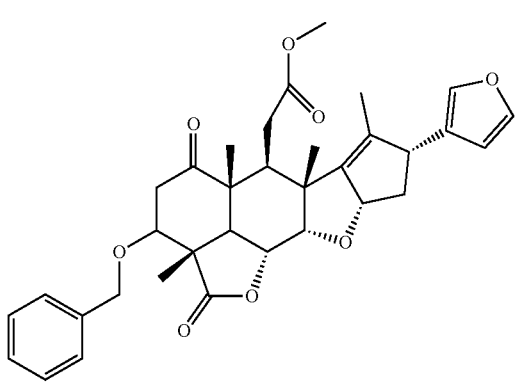

3

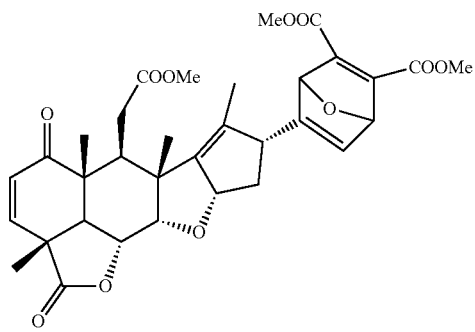

4

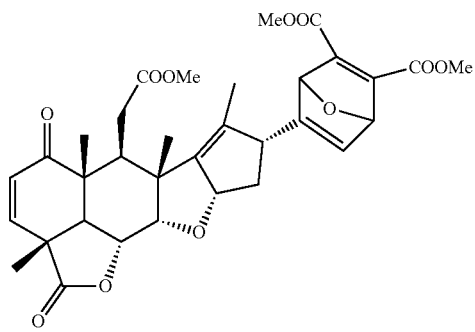

5

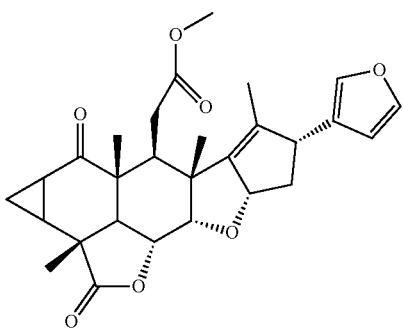

6

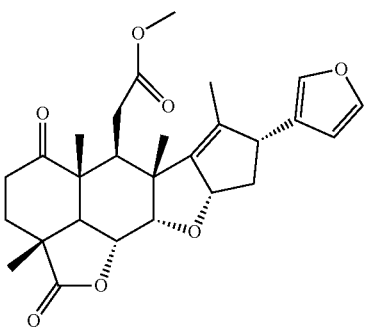

7

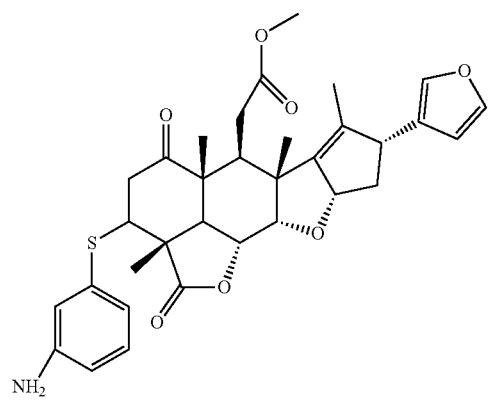

-continued

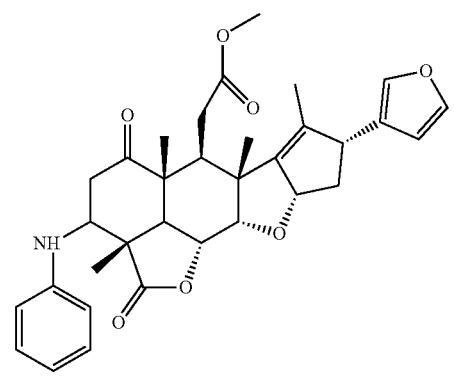

8

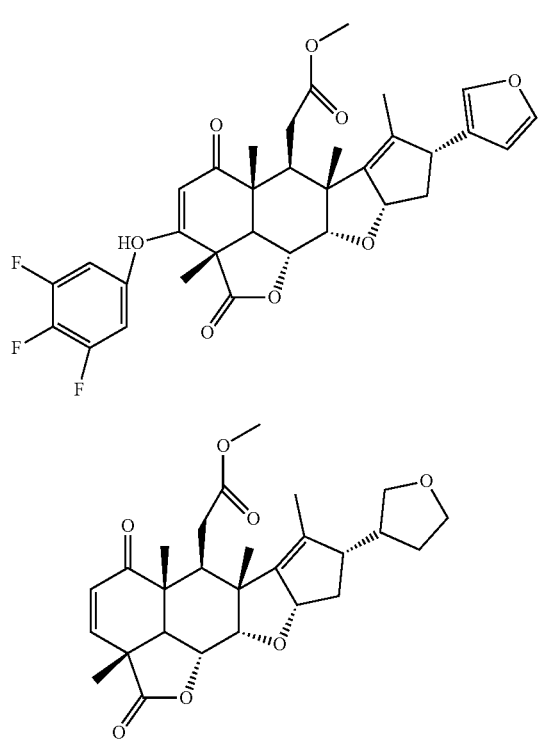

9

10

In another preferred embodiment the salts include salts of basic or acidic groups present in compounds of formula I wherein the basic salts are selected from the group consisting of aluminum, calcium, lithium, magnesium, potassium and sodium and acidic salts are selected from the group consisting of hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate and p-toluenesulfonate.

In another embodiment, the present invention provides a pharmaceutical composition comprising of the compound of general formula I along with pharmaceutically acceptable excipients.

In a preferred embodiment the excipients are selected from the group consisting of sucrose, lactose, xylitol, starch, sorbitol, gelatin, magnesium stearate, carboxymethyl cellulose, mint, cherry, fumed silica, magnesium carbonate, vegetable stearin, steric acid, methyl paraben, propyl paraben, retinyl palmitate, selenium, cysteine, methionine and citric acid.

In another embodiment, the present invention provides a process for the preparation of nimbolide analogs of formula I comprising the steps of:
a) treating nimbolide with an organic reagent selected from the group consisting of benzyl alcohol, nitrobenzaldehyde, trihalobenzaldehyde, aminothiophenol, dialkylacetylene dicarboxylate, trialkyllsulfoxonium iodide, sodium borohydride, lithium borohydride, sodium hydride and palladium on carbon, in an organic solvent optionally in presence of a base at a temperature in the range of −5 to 150° C. for a period in the range of 1-50 h;
b) purification of the product.

In a preferred embodiment the base is selected from the group consisting of 1,8-Diazabicyclo[5.4.0]undec-7-ene (DBU), imidazole, trimethylamine, pyridine, NaOH, KOH, NaHCO$_3$, K$_2$CO$_3$, NH$_4$Cl, Na$_2$SO$_4$ and NiCl$_2$.6H$_2$O In a preferred embodiment the organic solvent is selected from the group consisting of ethers, alcohols, toluene, dimethylformamide, dimethylsulfoxide, dioxin, esters, chlorinated organic solvents, hexane, pentane, heptane and acetonitrile.

In another embodiment, the present invention provides a method of treatment of cancer using the compound of general formula I or the composition comprising the compound of general formula I.

In another preferred embodiment the nimbolide are useful as anti-cancer agents.

A large number of various nimbolide derivatives possessing diversely substituted architecture were found to exhibit several biological properties. These functionalities are prominent structural motifs of new medicines from different pharmacological groups. The development of new structural scaffolds of nimbolide architecture is very important for the drug discovery process. In this connection a large number of nimbolide derivatives were developed as depicted in the general formula I. The processes for the synthesis of these new nimbolide derivatives involve operationally simple and highly efficient synthetic protocol giving rise to the desired products in high yields. The synthesis of these compounds has been carried out by simple functional group modification of basic nimbolide core.

Biological Activity

The nimbolide derivatives prepared are tested for anti-cancer activity and in this study, we demonstrate that IM-1372-Kn-13 (A4) is effective in inhibiting the growth of pancreatic cancer cells in culture as well as in the in vivo model. Our results reveal that IM-1372-Kn-13 treatment arrested tumor growth and also tumor volume is reduced in pancreatic cancer xenograft model according to test compound dose injected intratumorolly. Further, IM-1372-Kn-13 did not show any effect on the other tissues of xenograft mice. On the other hand IM-1372-Kn-13 failed to show any toxic effects up to 50 mg/kg in acute toxicity studies. We also observed that the suppression of pancreatic cancer tumor growth by IM-1372-Kn-13 is due to induction of apoptosis. These findings should be conformed in the clinical settings in pancreatic cancer patients.

DETAILED DESCRIPTION OF THE INVENTION

Figure 1:
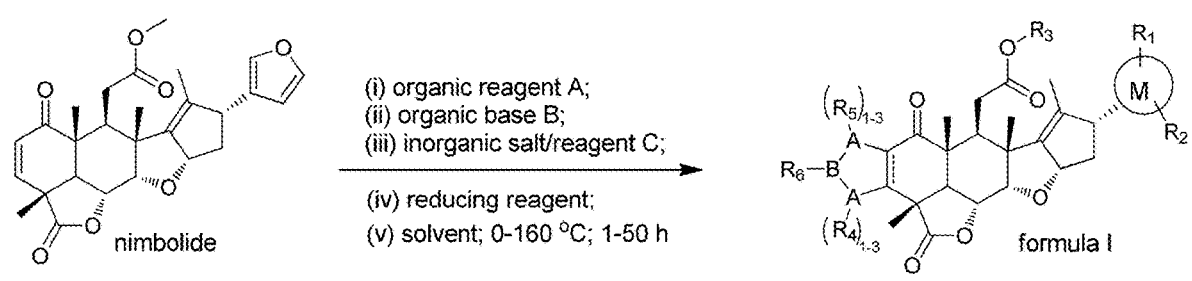
FIG. 1: Synthesis of nimbolide analogs of general formula I

Nimbolide and its analogs are efficient structural motifs capable of showing diverse biological activities. This resulted in design and synthesis of a number of novel nimbolide analogs, comprising the following steps and purification:
a) treating nimbolide with one or more of these: organic reagent A, organic base B, reducing reagent C in organic solvent/s at −5 to 160° C. for a period in the range of 1-50 h;
b) monitoring of the reaction by thinlayer chromatography or HPLC methods; c) reaction workup using solvent extraction methods; d) purification of the product by column chromatography.

EXAMPLES

The present invention will be more specifically explained by following examples. However, the scope of the present invention is not limited to the scope of the examples stated below.

Example 1: To a solution of nimbolide (0.1 g, 0.21 mmol, 1 eq) in benzyl alcohol (1 mL) in reaction vessel was added DBU (0.016 mL, 0.10 mmol) via a syringe. After stirring for 15 h, the reaction mixture was diluted with ether (5 mL) and washed with sat. $NH_4Cl$ (5 mL). The organic extracts were dried over $Na_2SO_4$ and the solvent removed to afford the crude compound. The crude residue was purified by silica gel column chromatography gave the product as white solid. HRMS (m/z): $[M+Na]^+$ calcd for $C_{34}H_{38}Na\ O_8$ 597.2562, found 597.2523. $^1H$ NMR ($CDCl_3$, 300 MHz): δ 7.38-7.29 (m, 6H), 6.35 (s, 1H), 5.56-5.53 (m, 1H), 4.67 (s, 2H) 4.54 (dd, J=12.2, 3.4 Hz, 1H), 4.23 (d, J=3.2 Hz, 1H), 4.01 (brs, 1H), 3.66 (d, J=8.30, 2H), 3.54 (s, 3H), 3.48 (d, J=12.4, 1H), 2.80-2.89 (m, 2H), 2.89-2.80 (m, 2H), 2.76-2.71 (m, 1H), 2.47 (dd, J=16.05, 1H), 2.38-2.30 (m, 2H), 2.27-2.18 (m, 1H), 2.16-2.08 (m, 1H), 1.70 (s, 3H), 1.46 (s, 3H), 1.33 (s, 3H), 1.25 (s, 3H).

Example 2: To a stirred mixture nimbolide (0.1 g, 0.21 mmol, 1 eq) and 4-Nitrobezaldehyde (0.065 g, 0.429 mmol, 2 eq) in THF (1 mL), imidazole (0.014 g, 0.21 mmol, 1 eq) and 1M $NaHCO_3$ (0.8 mL) was added. The mixture was stirred for 48 h at ambient temperature and monitored by TLC. Upon completion or reaction was extracted with ethyl acetate (3 mL×3). The organic layer was dried over anhydrous $Na_2SO_4$, filtered and concentrated under reduced pressure. The residue was purified by silica gel column chromatography to give the desired product. HRMS (m/z): $[M+Na]^+$ calcd for $C_{34}H_{35}Na\ O_{10}$ 640.2153, found 640.2205. $^1H$ NMR ($CDCl_3$, 400 MHz): δ 8.23 (d, J=8.6 Hz, 1H), 7.53 (d, J=8.6 Hz, 1H), 7.34-7.30 (m, 1H), 7.20-7.18 (m, 1H), 7.15 (s, 1H), 6.22-6.19 (m, 1H), 5.67 (d, J=3.9 Hz, 1H), 5.52-5.43 (m, 1H), 4.61 (dd, J=12.2, 3.5 Hz, 1H), 4.26 (d, J=3.3 Hz, 1H), 3.67 (d, J=8.3 Hz, 1H), 3.51 (s, 3H), 3.20-3.05 (m, 2H), 2.68 (t, J=5.4 Hz, 1H), 2.35 (dd, J=16.4, 5.4 Hz, 1H), 2.26-2.04 (m, 2H), 1.70 (s, 3H), 1.61 (s, 3H), 1.36 (s, 3H), 1.21 (s, 3H).

Example 3: To a solution of nimbolide (300 mg, 0.643 mmol, 1 eq) in Toluene 10 mL (sealed tube) dimethylacetylene dicarboxylate (0.95 mL, 0.772 mmol, 1.2 eq) was added and heated to 150° C. for 40 h. After completion of reaction the reaction mixture was concentrated and purified by silica gel column chromatography using EtOAc in hexane (60:40) gave the product as white solid (280 mg, 71.6% yield). HRMS (m/z): $[M+Na]^+$ calcd for C33 H36NaO11- 608.2258, found 608.2202; $^1H$ NMR ($CDCl_3$, 400 MHz): δ 7.28 (d, J=9.6 Hz, 1H), 6.66 (d, J=1.8 Hz, 1H), 5.94 (d, J=9.6 Hz, 1H), 5.52 (t, J=1.8 Hz, 1H), 5.51-5.47 (m, 1H), 4.61 (dd, J=12.5, 3.6 Hz, 1H), 4.24 (d, J=3.6 Hz, 1H), 3.84 (s, 3H), 3.81 (s, 3H), 3.63 (s, 3H), 3.59 (d, J=9.3 Hz, 1H), 3.32 (dd, J=16.4, 4.5 Hz, 1H), 3.21-3.11 (m, 2H), 2.76 (dd, J=6.4, 4.7 Hz, 1H), 2.41 (dd, J=16.3, 6.5 Hz, 1H), 2.17 (dd, J=12.6, 6.5 Hz, 1H), 1.99-1.91 (m, 1H), 1.65 (s, 3H), 1.47 (s, 3H), 1.37 (s, 3H), 1.22 (s, 3H).

Example 4: Sodium hydride (60 percent oil dispersion, 20 mg, 0.515 mmol) was added to a stirred solution of trimethylsulfoxonium iodide (113 mg, 1.1 mmol) in DMSO (0.5 mL) under a nitrogen atmosphere, After 30 minutes a solution of nimbolide (60 mg, 0.12 mmol) in dry Tiff (1 mL) was added. After 2.5 h the reaction mixture was poured into ice-water and extracted with ethyl acetate. The combined organic layers were washed with brine, dried over sodium sulphate and the solvents were evaporated in vacuo. The crude product was purified by silica gel column chromatography gave a white solid compound (46 mg, 75%); HRMS (m/z): $[M+Na]^+$ calcd for $C_{28}H_{32}Na\ O_7$ 503.2046, found 503.2073; $^1H$ NMR ($CDCl_3$, 300 MHz): δ 7.31-7.29 (m, 1H), 7.25 (d, J=9.6 Hz, 1H), 7.20 (s, 1H), 6.24 (s, 1H), 5.91 (d, J=9.7 Hz, 1H), 5.54-5.47 (m, 1H), 4.61 (dd, J=12.4, 3.6 Hz, 1H), 4.25 (d, J=3.5 Hz, 1H), 3.65 (d, J=8.5 Hz, 1H), 3.52 (s, 3H), 3.24 (dd, J=16.2, 5.2 Hz, 1H), 3.16 (d, J=12.4 Hz, 1H), 2.72 (t, J=5.5 Hz, 1H), 2.36 (dd, J=16.2, 5.8 Hz, 1H), 2.24-2.16 (m, 1H), 2.15-2.05 (m, 1H), 1.69 (s, 3H), 1.46 (s, 3H), 1.35 (s, 3H), 1.21 (s, 3H); $^{13}C$ NMR ($CDCl_3$, 125 MHz): δ 227.5, 195.8, 191.3, 163.2, 161.5, 157.1, 154.7, 144.8, 128.5, 106.7, 101.7, 91.0, 70.1, 68.5, 67.9, 64.3, 60.4, 59.6, 58.8, 58.7, 50.0, 48.0, 43.3, 41.9, 38.2, 35.8, 34.7, 31.2, 30.9.

Example 5: To a solution of nimbolide (0.1 g, 0.2 mmol, 1 eq) in methanol (5 mL), $NiCl_2.6H_2O$ (0.25 g, 1.0 mmol, 5 eq) was added and cooled to 0° C., $NaBH_4$ (0.016 g, 0.429 mmol, 2 eq) was added and allowed it to rt for 3 h. After completion of reaction quenched with aq. ammonium chloride, concentrated and extracted the product with ethyl acetate. The crude residue was purified by silica gel column chromatography gave a product as white solid; HRMS (m/z): $[M+H]^+$ calcd for C27 H3307- 469.2221, found 469.2239; $^1H$ NMR ($CDCl_3$, 400 MHz): δ 7.33 (t, J=1.6 Hz, 1H), 7.26-7.24 (m, 1H), 6.33-6.32 (m, 1H), 5.55-5.50 (m, 1H), 4.55 (dd, J=12.0, 3.5 Hz, 1H), 4.21 (d, J=3.5 Hz, 1H), 3.66 (d, J=8.5 Hz, 1H), 3.56 (s, 3H), 2.86 (dd, J=15.7, 5.1 Hz, 1H), 2.82-2.76 (m, 1H), 2.71-2.66 (m, 1H), 2.40-2.34 (m, 3H), 2.32 (dd, J=15.7, 5.7 Hz, 1H), 2.22 (dd, J=12.2, 6.5 Hz, 1H), 2.13-2.07 (m, 3H), 1.69 (s, 3H), 1.50 (s, 3H), 1.33 (s, 3H), 1.28 (s, 3H); $^{13}C$ NMR ($CDCl_3$, 125 MHz): δ 210.4, 177.7, 172.9, 145.0, 143.0, 138.9, 136.0, 126.5, 110.4, 88.3, 82.7, 72.7, 51.7, 50.0, 49.6, 49.4, 49.3, 41.2, 40.8, 34.4, 33.2, 32.9, 17.1, 15.7, 15.1, 12.8.

Example 6: To a solution of nimbolide (0.1 g, 0.21 mmol, 1 eq) and 3-amino thiophenol (0.027 mL, 0.25 mmol, 1.2 eq) in methanol (1 mL) in reaction vessel was added $Et_3N$ (0.08 mL, 0.63 mmol, 3 eq) via a syringe. After stirring for overnight, the reaction mixture was diluted with ether (5 mL) and washed with sat. $NH_4Cl$ (5 mL). The organic extracts were dried over $Na_2SO_4$ and the solvent removed to afford the crude compound. The crude residue was purified by silica gel column chromatography gave the product as white solid; HRMS (m/z): $[M+H]^+$ calcd for $C_{33}H_{38}N\ O_7$ S 591.2363, found 591.2395; $^1$H NMR (CDCl$_3$, 400 MHz): δ 7.34 (t, J=1.5 Hz, 1H), 7.28-7.27 (m, 1H), 7.08 (t, J=7.8 Hz, 1H), 6.93 (dq, J=7.5, 0.9 Hz, 1H), 6.90 (t, J=2.0 Hz, 1H), 6.60 (dq, J=7.9, 0.8 Hz, 1H), 6.36-6.34 (m, 1H), 5.64-5.56 (m, 1H), 4.55 (dd, J=11.9, 3.4 Hz, 1H), 4.23 (d, J=3.3 Hz, 1H), 3.67 (d, J=8.4 Hz, 1H), 3.64 (dd, J=5.1, 1.9 Hz, 1H), 3.55 (s, 3H), 3.33 (d, J=12.1 Hz, 1H), 3.14 (dd, J=16.1, 5.1 Hz, 1H), 2.89 (dd, J=15.5, 5.0 Hz, 1H), 2.74 (t, J=5.9 Hz, 1H), 2.54 (dd, J=16.1, 2.0 Hz, 1H), 2.34 (dd, J=15.5, 6.2 Hz, 1H), 2.27 (dd, J=12.2, 6.7 Hz, 1H), 2.17-2.08 (m, 1H), 1.70 (s, 3H), 1.61 (s, 3H), 1.34 (s, 3H), 1.27 (s, 3H); $^{13}$C NMR (CDCl$_3$, 100 MHz): δ 207.8, 175.1, 172.8, 147.0, 145.0, 143.0, 138.8, 135.8, 133.7, 129.8, 126.6, 124.1, 120.6, 115.0, 110.5, 88.4, 82.8, 72.7, 52.4, 51.7, 49.5, 49.4, 46.7, 44.8, 41.2, 40.8, 40.7, 32.9, 18.2, 17.1, 15.0, 12.9.

Example 7: To a solution of nimbolide (0.1 g, 0.21 mmol, 1 eq) in aniline (1 mL) in reaction vessel was added DBU (0.016 mL, 0.10 mmol) via a syringe. After stirring for overnight, the reaction mixture was diluted with ether (5 mL) and washed with sat. NH$_4$Cl (5 mL). The organic extracts were dried over Na$_2$SO$_4$ and the solvent removed to afford the crude compound. The crude residue was purified by silica gel column chromatography gave the product as white solid; HRMS (m/z): [M+Na]$^+$ calcd for C33 H37 N Na O7$^+$ 582.2462, found 582.2487; $^1$H NMR (CDCl$_3$, 400 MHz): δ 7.34 (t, J=1.7 Hz, 1H), 7.28-7.27 (m, 1H), 7.21-7.15 (m, 2H), 6.85-6.76 (m, 3H), 6.36-6.34 (m, 1H), 5.63-5.56 (m, 1H), 4.58 (dd, J=12.1, 3.5 Hz, 1H), 4.23 (d, J=3.4 Hz, 1H), 3.99 (brs, 1H), 3.74-3.64 (m, 1H), 3.67 (d, J=8.4 Hz, 1H), 3.54 (s, 3H), 3.22 (d, J=12.1 Hz, 1H), 3.16 (dd, J=15.6, 4.8 Hz, 1H), 2.83-2.72 (m, 2H), 2.48 (dd, J=15.6, 2.2 Hz, 1H), 2.40-2.31 (m, 1H), 2.29-2.21 (m, 1H), 2.14-2.04 (m, 1H), 1.70 (s, 3H), 1.63 (s, 3H), 1.35 (s, 3H), 1.33 (s, 3H); $^{13}$C NMR (CDCl$_3$, 125 MHz): δ 209.6, 175.3, 173.0, 146.6, 143.0, 138.9, 136.1, 128.9, 126.5, 119.4, 115.6, 110.5, 88.3, 82.8, 72.5, 59.1, 51.7, 50.1, 49.5, 47.3, 44.5, 41.1, 40.8, 40.6, 32.9, 31.9, 22.6, 17.3, 17.1, 14.5, 12.9.

Example 8: To a stirred mixture nimbolide (0.1 g, 0.21 mmol, 1 eq) and 3,4,5-triflouoro benzaldehyde (0.068 g, 0.429 mmol, 2 eq) in THF (1 mL), imidazole (0.014 g, 0.21 mmol, 1 eq) and 1M NaHCO$_3$ (0.8 mL) was added. The mixture was stirred for 48 h at ambient temperature and monitored by TLC. Upon completion or reaction was extracted with ethyl acetate (3 mL×3). The organic layer was dried over anhydrous Na$_2$SO$_4$, filtered and concentrated under reduced pressure. The residue was purified by silica gel column chromatography to give the desired product; $^1$H NMR (CDCl$_3$, 400 MHz): δ 7.63-7.61 (m, 1H), 7.31 (m, 1H), 7.11 (m, 1H), 7.08 (s, 1H), 6.90-6.92 (m, 1H), 6.21-6.20 (m, 1H), 5.51-5.40 (m, 1H), 4.61 (dd, J=12.2, 3.5 Hz, 1H), 4.26 (d, J=3.3 Hz, 1H), 3.67 (d, J=8.3 Hz, 1H), 3.51 (s, 3H), 3.20-3.05 (m, 2H), 2.68 (t, J=5.4 Hz, 1H), 2.35 (dd, J=16.4, 5.4 Hz, 1H), 2.26-2.04 (m, 2H), 1.70 (s, 3H), 1.61 (s, 3H), 1.36 (s, 3H), 1.21 (s, 3H).

Example 9: To a stirred solution of nimbolide (0.1 g, 0.21 mmol, 1 eq) in MeOH Pd—C was added and kept under hydrogen balloon at rt for overnight. After completion of reaction the reaction mixture filtered through celite pad and concentrated under reduced pressure and purified by silica gel column chromatography using 1:1 of EtOAc and hexane as mobile phase. The product obtained as a white solid (54 mg); $^1$H NMR (CDCl$_3$, 400 MHz): δ 5.41-5.33 (m, 1H), 4.53 (dd, J=12.2, 3.5 Hz, 1H), 4.17-4.14 (m, 1H), 3.90-3.83 (m, 2H), 3.75-3.69 (m, 1H), 3.68 (s, 3H), 3.41-3.30 (m, 2H), 2.87-2.82 (m, 1H), 2.82-2.75 (m, 1H), 2.64 (d, J=12.0 Hz, 1H), 2.62-2.56 (m, 1H), 2.39-2.25 (m, 3H), 2.20-2.16 (m, 1H), 2.12-1.92 (m, 4H), 1.92-1.84 (m, 1H), 1.79 (d, J=1.5 Hz, 1H), 1.72 (d, J=1.5 Hz, 1H), 1.58 (s, 3H), 1.49 (s, 3H), 1.31 (s, 3H), 1.27 (s, 3H); $^{13}$C NMR (CDCl$_3$, 100 MHz): δ 210.5, 177.9, 173.0, 147.0, 145.2, 136.2, 87.2, 82.4, 72.8, 72.4, 67.9, 55.8, 51.7, 50.1, 49.6, 49.4, 42.2, 40.8, 40.7, 37.8, 34.4, 33.3, 32.8, 31.3, 17.1, 15.8, 15.2, 13.4.

Biological Activity and Screening: Materials & Methods:

Cell culture: Human lung adenocarcinoma cell line (A549 cell line), pancreatic cancer cell line (Panc-1, Pan-02), prostate cancer cell line (DU145, PC3), Brest cancer cell line (MCF-7) was grown in DIEM (Dulbecco's modifications of eagle's medium with L-glutamine & 4.5 g/L glucose) supplemented with fetal bovine serum in a humidified atmosphere of a 5% CO$_2$ at 37° C.

Chemicals: Sulforhodamine B, Doxorubicin, DMSO, 1% Acetic acid, 10 mM Tris, SDS, Acrylamide, bis-acrylamide, RIPA buffer (50 mM-tris (PH-7.4), 150 mM-Nacl, 1% NP-40, 0.1% SDS, 0.5% Sodium-deoxycholate, 1 mM EDTA, 5 mM NaF, 5 mM-Na—O-vandate, 1 mM PMSF, Protease inhibitor cocktail), Caspase assay buffer (20 mM HEPES, 2 mM EDTA, 0.1% CHAPS), Ac-DEVD AMC (caspase-3)/Ac-VETD-AMC (caspase-8)/Ac-VETD-AMC (caspase-9). All chemicals are purchased from sigma chemicals.

In vitro anticancer activity: Cells were harvested from exponential phase cultures by trypsinization, counted and plated in 96-well plate. Optimal seeding densities for different cell lines in each plate were 5000 cells per well. After 24 h cells were treated with \ the newly synthesized compound at a dose range of 0.1-100 μm final concentration. Thereafter, cells were allowed to grow for 48 h before determination of cell survival by the SRB assay. Then the cells were fixed with 10% cold trichloroacetic acid for 1 h at 4° C. After two washes with deionized water, fixed cells were stained with 50 μL of SRB solution (1% in acetic acid) for 30 min and subsequently washed twice with 1% acetic acid to remove unbound stain. The plates were left to dry at room temperature and bound stain was solubilized with 100 μL of 10 mM buffered Tris base for reading the optimal density at 540 nm.

Western blotting analysis of IM-1372-Kn-13 on Panc-1 cell line: The cells were lysed in RIPA buffer (50 mM-tris (PH-7.4), 150 Min-Nacl, 1%-NP-40, 0.1%-SDS, 0.5%-Sodium-deoxycholate, 1 mM EDTA, 5 mM NaF, 5 mM Na—O-vandate, 1 mM PMSF, Protease inhibitor cocktail). The lysates were cleared by centrifugation at 14,000×10 min and concentration of protein was estimated by bradford assay. For Western blot analysis, equivalent amount of protein was resolved in SDS-PAGE and then transferred to polyvinylidene difluoride (PVDG) membrane. Ti avoid non specific binding of antibodies, the membranes were blocked using 3% BSA in TBS with 0.5% Tween (TBST) for 1 h at room temperature. The membranes were then incubated in primary antibody overnight at 4° C. After removing excess primary antibody bound to membranes, blots were incubated with secondary anti body. Then the signal emitted was captured using chemiluminescence substrate.

Caspase assay activity: Caspase-3, caspase-8 and caspase-9 protease activities were determined using a commercial fluorescence assay kit according to the manufacturer's instructions, Briefly, pancreatic cancer cells were treated with different concentrations of IM-1372-Kn-13 for 24 h were re-suspended in 50 μL of chilled cell lysis buffer; cells were then incubated on ice for 10 min and centrifuged for 1 min in a micro-centrifuge (10,000 g). Then supernatants were transferred (cytosolic extract) to a fresh tube and protein concentration was assayed. Next, diluted 100 μg protein was added to 50 μL cell lysis buffer for each assay.

Subsequently, 50 μL of 2× reaction buffer and 5 μL of the 4 mM Ac-DEVD AMC (caspase-3)/Ac-VETD-AMC (caspase-8)/Ac-VETD-AMC (caspase-9) were added and incubated at 37° C. for 2 h (samples read at 405 nm in a microtiter plate reader).

RESULTS: In vitro anticancer activity: The newly synthesized compounds along with reference nimbolide were evaluated for its cytotoxic activity in vitro against seven cancer cell lines DU-145, A549, MCF-7, PC3, Panc-1, NIH3T3, and Pan-02 by employing SRB assay. The activity results obtained revealed that, these compounds exhibited different levels of anticancer properties (Table 1). From the close analysis of the $IC_{50}$ values, it was observed that, the IM-1372-Kn-13 (A4) showed cancer cell growth inhibition against DU-145, A549, MCF-7, PC3, Panc-1, and Pan-02 while no activity was observed in NIH3T3 cells.

IM-1372-Kn-13 induced apoptosis in pancreatic cancer cells, the expression of typical apoptosis-related proteins p27, p53, and p21 were analysed by Western blot. As shown in FIG. 2D, the p21, p27, p53 proteins were reduced in IM-1372-Kn-13-treated cells. FIG. 2D: Effect of IM-1372-Kn-13 on expression of p21, p2′7, p53 in panc-1 cells. Cells were treated with various Concentrations of IM-1372-Kn-13 for 24 h. Western blots for each protein were done at least twice using independently prepared lysates.

In vivo studies: Materials and methods: Animals and cell lines: Healthy 8-10 week old nude mice of either sex, weighing between 20 g and 25 g were used as experimental animals for tumor induction. All animals were maintained under standardized animal house conditions (12 h light and 12 h dark condition) at controlled temperature (22±1° C.) and relative humidity (60-70%) in institutional registered

TABLE 1

Cytotoxic effect of series of nimbolide analogues (A2 to A10) against panel of cancer cells

| Cell line | $IC_{50}$ A2 | $IC_{50}$ A3 | $IC_{50}$ A4 | $IC_{50}$ A5 | $IC_{50}$ A6 | $IC_{50}$ A7 | $IC_{50}$ A8 | $IC_{50}$ A9 | $IC_{50}$ A10 |
|---|---|---|---|---|---|---|---|---|---|
| DU 145 | 1.45 | 9.31 | 0.58 | 7.91 | 75.1 | NA | NA | 16.83 | NA |
| A549 | 13.09 | 12.21 | 4.54 | 60.82 | 67.20 | 23.87 | 89.44 | 38.71 | 58.66 |
| pc3 | 1.01 | 9.08 | 1.40 | 20.56 | 79.07 | 65.35 | 20.97 | NA | NA |
| MCF-7 | 4.72 | 4.74 | 12.52 | 17.05 | 32.45 | 52.17 | 56.55 | 43.61 | 24.10 |
| panc-1 | 8.78 | 7.79 | 9.08 | 1.04 | 32.86 | 18.59 | 85.54 | 39.27 | 29.75 |
| NIHT3T3 | NA | NA | NA | NA | NA | NA | NA | NA | NA |
| Pan-02 | ND | ND | 0.52 | ND | ND | ND | ND | ND | ND |

NA—Not Active,
ND—Not Determined

Activation of caspase-3, -8 and -9 in IM-1372-Kn-13-induced apoptosis: Recent studies have identified caspases as important mediators of apoptosis induced by various apoptotic stimuli. Therefore, we examined the activity of caspase-3, -8 and -9 in Panc-1 cells treated with IM-1372-Kn-13 by fluorimetric assay. In addition to executioner caspase-3, initiator caspase-8 and -9 also plays a crucial role in apoptosis. The activities of caspase-3, -8 and -9 were increased significantly in a dose-dependent manner after treatment with IM-1372-Kn-13 (FIGS. 2A, 2B, and 2C), thus confirming that activated caspase mediates apoptosis in pancreatic cancer cells upon stimulation with IM-1372-Kn-13. All experiments were carried out in triplicates and mean values are presented in figures. FIG. 2A: Activation of caspase 3 was observed in cells treated with compound IM-1372-Kn-13, after incubation period of 48 h, it was seen that this compound cause activation of caspase 3. Doxorubicin was used as control for activation of caspases. All experiments were carried out in triplicates and mean values are presented here. FIG. 2B: Activation of caspase 8 was also observed in cells treated with compound IM-1372-Kn-13, after incubation period of 48 h, it was seen that this compound cause activation of caspase 8. Doxorubicin was used as control for activation of caspases. All experiments were carried out in triplicates and mean values are presented here. FIG. 2C: Relative activation of caspase 9 in cells treated with compound IM-1372-Kn-13 respectively. Upon 48 h of incubation it was seen that activation of caspase 9 occurs with increasing concentrations of the compounds. Doxorubicin was used as control for activation of caspases. All experiments were carried out in triplicates and mean values are presented here.

The effect of IM-1372-Kn-13 on the expression of p27, p53, and p21: To further investigate the molecular basis for animal house that was approved by Committee for the Purpose of Control and Supervision of Experiments on Animals (CPCSEA). They were maintained with standard pellet diet and water ad libitum. The institutional animal ethics committee approved the experimental protocol. CPCSEA guidelines were adhered to during the maintenance of animals and experiments. Pancreatic cancer cell line (Pan-02) was obtained from American Type Culture Collection and was cultured in RPMI medium.

Acute toxicity test: Safety tests begin with acute toxicity testing, where the animals are given a single dose of the test compound. The aim of the tests is to determine the range between the dose that causes no adverse effect and the dose that is life-threatening. Legislative guidance suggests that the effects on test animals should be compared with the effects on control groups of animals that have not received the compound. Different doses (50, 25, 10, and 5 mg/kg body weight) of the test compound are given to the animals separately through IP injection. Post injection, the animals were monitored for the first 4 h and observed at every hourly interval for next 24 h. Further, animals were observed everyday for 14 days for any signs of toxic effects and behavior of animals. On day 14 all the surviving animals are sacrificed by a humane method and dissected to investigate signs of toxicity internally. The results of these tests allow further studies to be planned, as they give information about the dosage that should be used, and how toxicity may occur. Compounds that are found to be toxic are not necessarily abandoned, as the degree of allowable toxicity will depend on the intended medical application. If the drug is intended for the treatment of life-threatening diseases, toxicity is less of a concern than in a drug intended for use in healthy individuals.

Establishment of Pancreatic cancer xenograft model: To establish tumor in mice, Pan-02 cells ($7 \times 10^6$) were suspended in 1:1 RPMI medium mixed with matrigel and subcutaneously implanted on right flank of the each mice. The injection sites were examined daily for the appearance of tumors. On $10^{th}$ day these animals were randomized and divided into 3 groups (6 mice in each group). Group I served as control group received 20% ethanol three times in a week. Test group animals in Group II and III received intratumoral injection of IM-1372-Kn-13 at 10 mg and 25 mg/kg body weight respectively three times in a week. All groups received 5 repeated doses in 12 days. Mice were weighed and tumor volumes were measured 3 times a week by Vernier caliper. Tumor volume in individual mice was calculated by the following formula. $0.5 \times L \, (W)^2$, Where L is length, W is width of the tumor. The control group animals were euthanized when tumor volume is reached heavier to animal. One-week after completion of treatment period, the animals were sacrificed, and tumors were excised, fixed, and embedded in paraffin. At the end of treatment, blood samples were collected to perform clinical biochemistry.

Histopathological examination: For pathological studies, 5 μm sections of formalin-fixed, paraffin-embedded tissue were prepared and stained with haematoxylin and eosin. After haematoxylin-eosin (HE) staining, the slides were observed and the images were taken using optical microscope (Axioplan-II imaging). All slides were reviewed in a blinded fashion by a single pathologist and assessed for the presence of necrotic lesions (nodules) in the tumors and organs of different groups of mice.

Biochemical analysis: In acute toxicity experiment, blood samples were collected from all the animals 1 week after the last dose and mice were sacrificed by cervical decapitation. The obtained serum was analyzed in clinical chemistry for the assessment of liver function tests (LFT), activity of serum alkaline phosphatase (ALP), alanine aminotransferase (ALT), aspartate aminotransferase (AST), kidney function tests (RFT) (serum urea and creatinine). The same tests were performed for serum samples collected from three groups of tumor xenograft mice used for determining in vivo activity of test compound against pancreatic cancer. The measurement of these biochemical parameters was done in Clinical Biochemical analyzer (Tulip coralab 3000™).

Statistical analysis: Statistical analysis was carried out using graph pad in stat software (version 6). The values were expressed as mean±standard error (SE). The p values <0.05 was considered as statistically significant.

RESULTS: Anti-tumor activity: In pancreatic cancer xenograft mouse model IM-1372-Kn-13 inhibited tumor growth and effectively reduced tumor volume compared to control group. We also observed effect of test compound in concentration dependent manner. Based on the in vitro results, we next examined whether these results could be translated into an in vivo xenograft mouse model. Administration of IM-1372-Kn-13 (10 mg/kg, 25 mg/kg body weight, intratumoral) in Nude mice did not cause any loss in body weight and food intake suggesting no apparent toxicity. IM-1372-Kn-13 treatment prevented the growth of Pan-02 cells xenograft tumors in Nude mice as determined by a significant decrease in tumor volume (FIG. 2e and Table 2) compared to vehicle-treated animals. The average volume of tumors in vehicle-treated animals reached the targeted volume 646.59±87.42 mm$^3$ after 28 days of post-inoculation. The average volume of tumors in test group is significantly decreased by IM-1372-Kn-13 (p<0.0001). From these results, we conclude that IM-1372-Kn-13 showed anticancer potential to prevent the tumorigenicity of Pan-02 cells in nude mice. FIG. 2e: Tumor volume (mm3) in different groups of mice, Bar graph indicates reduction in tumor volume by test compound.

TABLE 2

| S. No. | Control | IM-1372-Kn013 | |
| --- | --- | --- | --- |
| | | 10 mg/kg | 25 mg/kg |
| Tumor Volume (mm$^3$) | 646.594 ± 87.4 | 181.306 ± 12.7 | 109.46 ± 7.1 |

Figure 2:
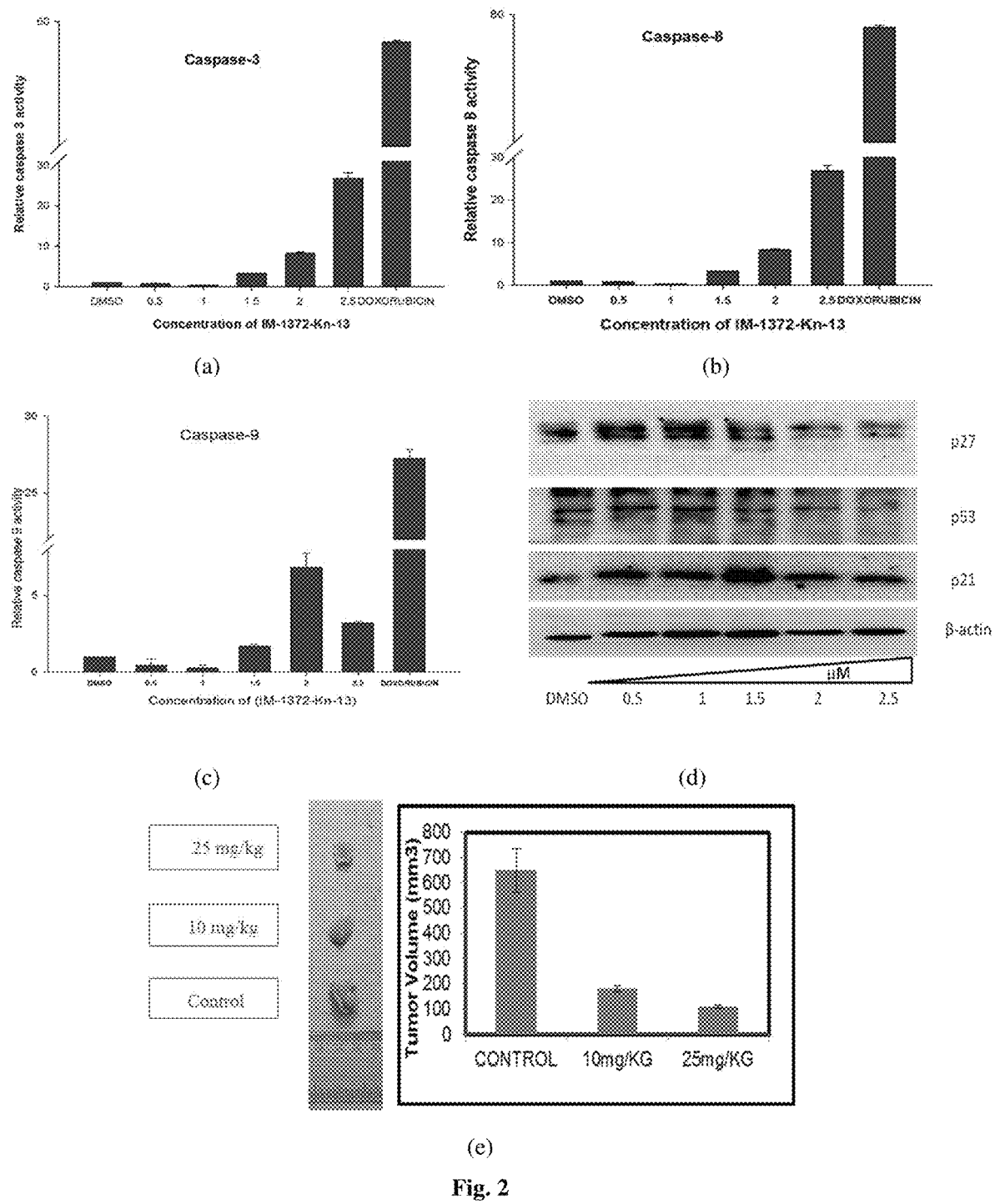
FIG. 2: In vitro anticancer activity studies (1a-d) and anti-tumor activity (1e)
Figure 3:
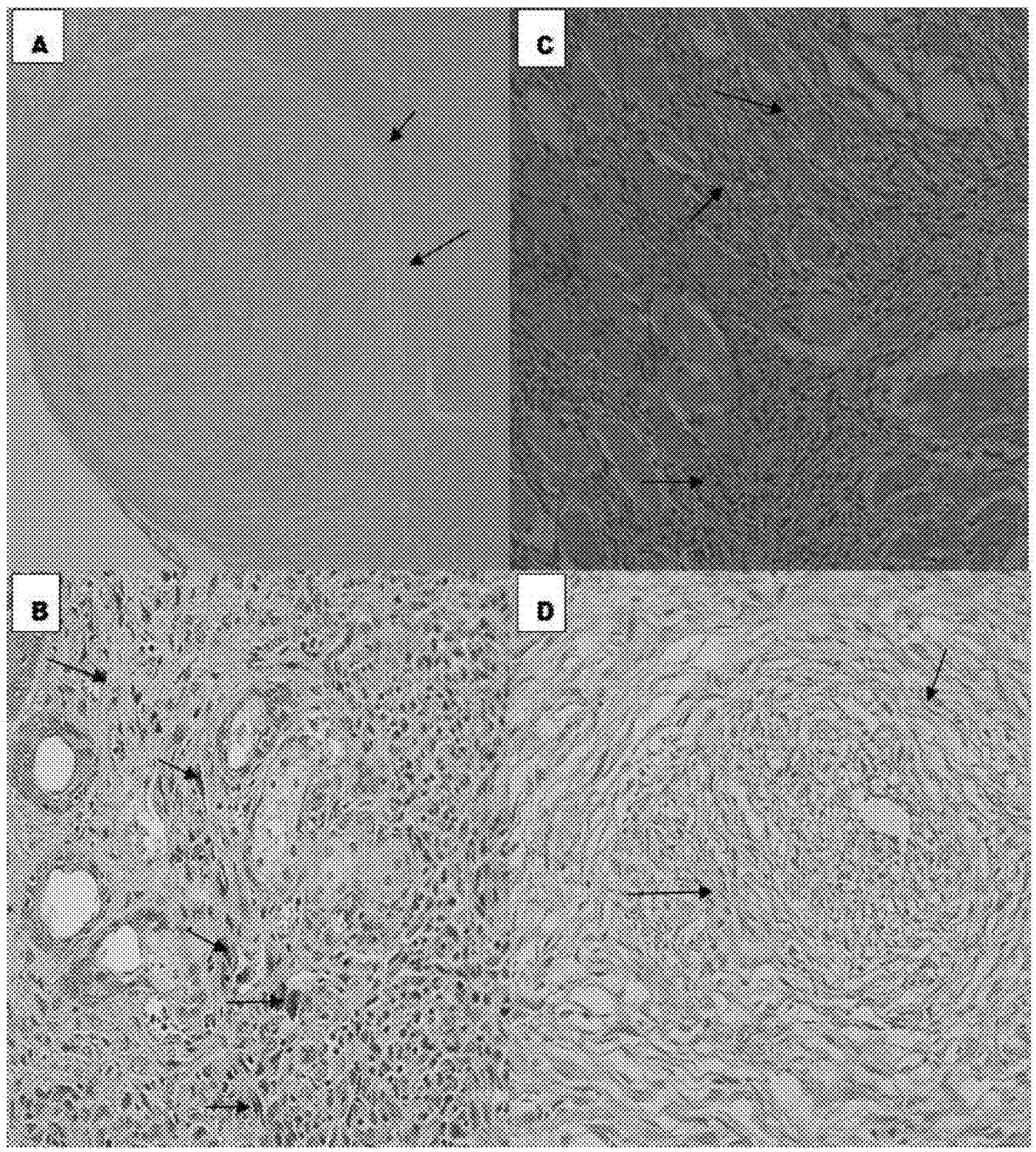
FIG. 3: Histopathological observation
Figure 4:
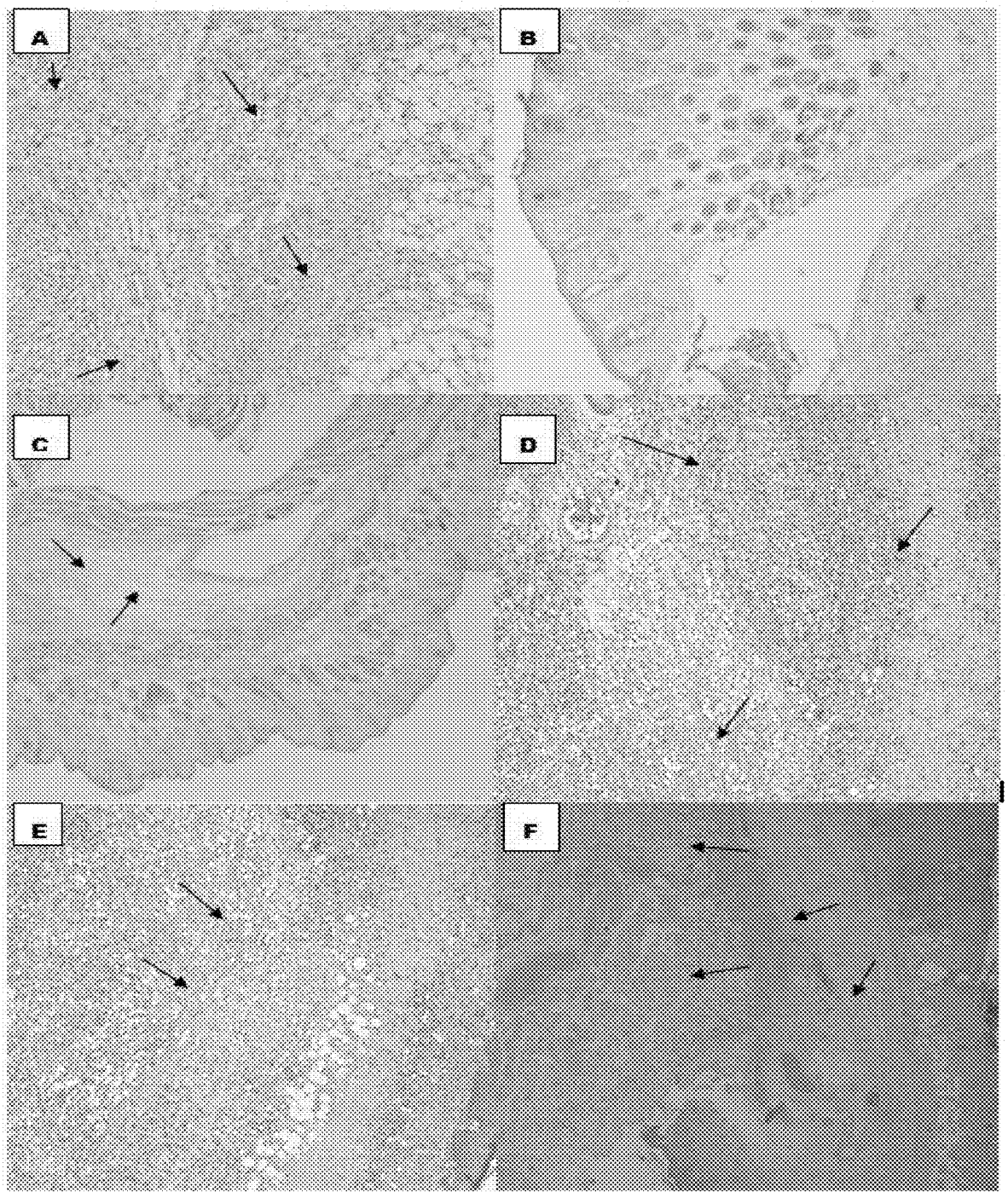
FIG. 4: Histopathological observation

Histopathological observation: In the Control group mice neoplastic cells formed a nodular type of mass [FIG. 3: A] in the subcutaneous region. These neoplastic cells moved to the dermis region [FIG. 3: B]. In some of the control animals neoplastic cells entered in to the epidermal layer of skin as well as muscular region [FIG. 3: C]. We could not find any kind of degeneration or necrosis in the central core of tumor tissue or any other region of tumor. Neoplastic cells are fibro sarcoma type with high proliferative and invasive nature. High mitotic index observed in the tumor cells. Sarcomatous neoplastic cells appeared as strap pattern in the invasive place and the central core of the tumor [FIG. 3: D]. In group II animals treated with test compound (10 mg/kg body weight) most of the neoplastic cells showed necrosis and these necrotic foci were replaced by fibrous tissue [FIG. 4: A]. No invasion of neoplastic cells found in dermal and epidermal region of skin [FIG. 4: B] but 50% of animals showed muscular invasion [FIG. 4: C]. But no nodular formation of tumor cells was noticed. In group III animals treated with test compound (25 mg/kg body weight) complete necrosis and lysis of tumor cells the entire tumor was noticed [FIG. 4: D]. All necrosed and lysed neoplastic cells were replaced by fibrous tissue. There was no invasion of cancer cells in dermal and epidermal region of skin. Neoplastic cells invaded into the muscular region also necrosed and replaced with fibrous tissue [FIGS. 4: E and F]. FIG. 2: (A) Nodular formation of neoplastic cells (B) Invasion neoplastic cells [Strap cells] in dermal layer of skin (C) Muscular layer invasion of neoplastic cells (D) Invasive nature of strap cells; FIG. 4: (A) Necrotic tumor cells were replaced by fibrous tissue. (B) NO invasion of neoplastic cells in dermal and epidermal region. (C) Neoplastic tissue replaced by fibrous tissue and No muscular invasion. (D) Necrosis and lysis of neoplastic cells. (E) Necrosis and lysis of neoplastic cells in sub cutaneous region. (F) Most of the tumor mass is replaced by fibrous tissues.

Figure 5:
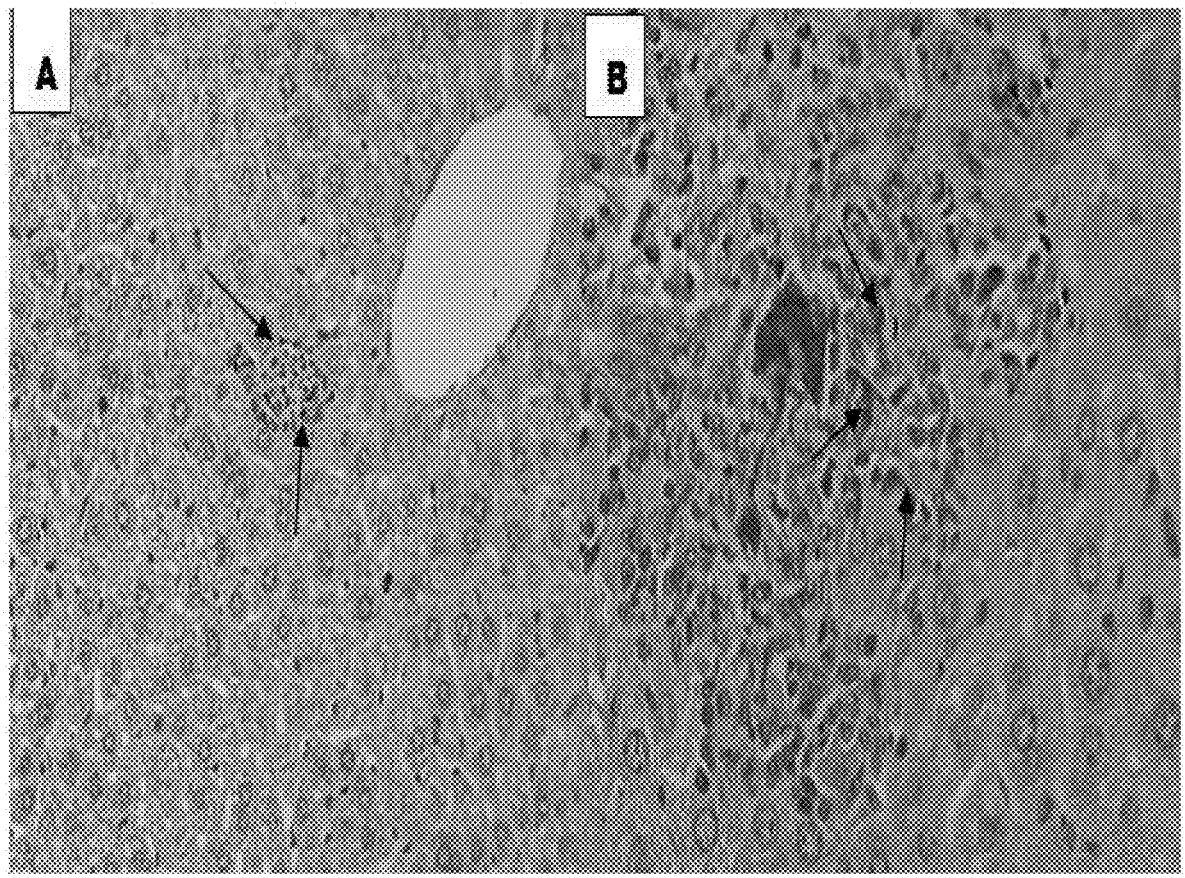
FIG. 5: Histopathological evaluation of other organs

Histopathological evaluation of other organs: In control group, 50% of mice showed metastasis in the liver. Neoplastic cells appeared as sarcomatous type and localized in peri-portal region of liver (FIG. 5: A). In group I, in only 10% of animals showed liver metastasis is appeared as sarcoma type with strap cells pattern in the centri-lobular region of liver (FIG. 5: B). In group II no metastatic invasion was found in liver, kidney and spleen. FIG. 5: Metastatic foci observed in the periportal region of liver. Neoplastic cells are sarcomatous type with strap pattern.

Figure 6:
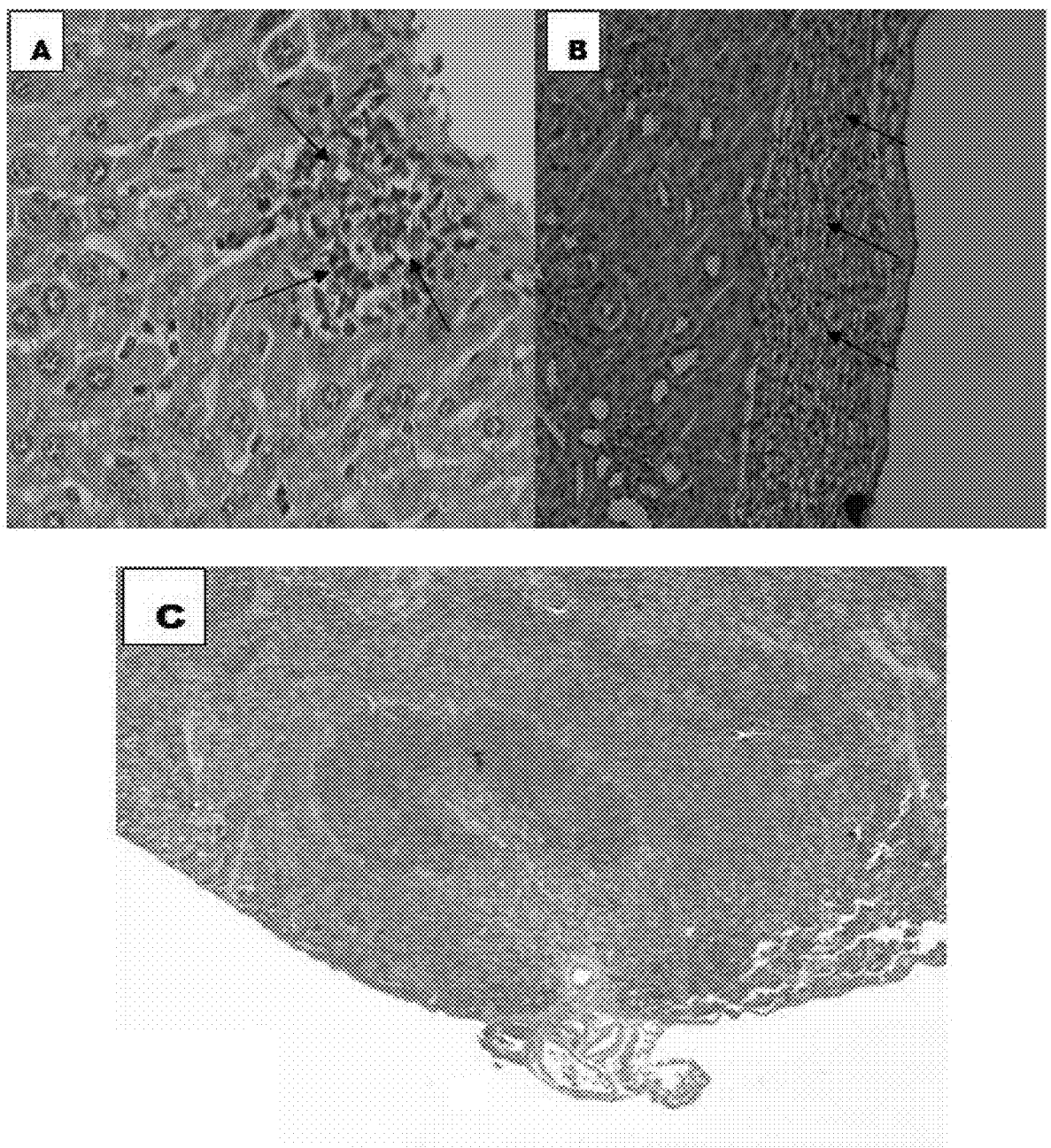
FIG. 6: Inflammation in the liver along with infiltration of inflammatory cells

Histopathology of tissues from acute toxicity study: Complete evaluation of organs and tissues did not show any indication of major destruction or loss. In mice injected with 50 mg/kg body weight we noticed a minor inflammation in the liver along with infiltration of inflammatory cells particularly lymphocytes in peri-portal region of liver (FIG. 6: A) and moderate capsular thickening and fibrosis in the renal capsules (FIG. 6: B). But glomerulus and tubular region appeared normal. The same observations were not found in mice treated with 25 mg/kg body weight, all organs including liver, kidney and spleen appeared normal (FIG. 6: C). FIG. 6: Inflammation in the liver along with infiltration of inflammatory cells.

Biochemical analysis: Liver function tests (LFTs) are commonly used to detect hepatic dysfunction where assay of serum AST, ALT and ALP are the most frequently used hepatocellular markers to analyze hepatocellular injury. In the present study, serum ALT, AST and ALP enzyme activities are significantly increased in group I. However these elevated enzyme activities are returned to normal in group II and group II animals. This result very well correlates with appearance of metastatic foci in control group animals (group I) where as no liver metastasis in test compound (IM-1372-Kn-13) treated animals. Surprisingly, serum total protein and albumin levels are significantly increased in group II and III compared control group I. This may be due to compromised liver function to some extent. Further, serum urea and creatinine levels were estimated to monitor the renal toxicity in the mice. Group I mice showed significant increase in serum urea and creatinine levels (Table 3). However, as compared to group I mice, in tumor-bearing mice treatment with IM-1372-Kn-13 significantly fetched down the elevated levels of serum urea and creatinine respectively (Table 3). Interestingly, in all groups serum glucose levels are varying with in the normal glucose levels (58 to 110 mg/dL). This may be due to metabolic activity of individual mice.

Biochemical analysis in acute toxicity studies: We observed a significant a significant increase in serum ALT, AST, levels in mice injected with test compound in a dose dependent manner. However, at lower concentration (effective dose for treating mice bearing tumors) the increase is not significant. Particularly, in mice injected with 50 mg/kg ALT and AST activity suggest that there is a sign of impaired hepatic and renal function due to test compound.

TABLE 3

Effect of test compound on clinical biochemistry pattern in control and test animals

|  | | IM-1372-Kn-13 | |
| --- | --- | --- | --- |
| Parameters | Control | Drug treated 10 mg/kg | Drug treated 25 mg/kg |
| Alkaline phosphatase (U/L) | 894.48 ± 32.4 | 685.26 ± 28.8 | 545.63 ± 24.9 |
| SGOT (U/L) | 93.35 ± 6.8 | 56.12 ± 5.8 | 32.20 ± 2.4 |
| SGPT (U/L) | 52.44 ± 7.6 | 47.05 ± 5.8 | 24.49 ± 4.0 |
| Total protein (g/dL) | 5.29 ± 0.4 | 6.24 ± 0.5 | 8.05 ± 0.3 |
| Albumin (g/dL) | 2.58 ± 0.2 | 3.16 ± 0.2 | 3.61 ± 0.1 |
| Urea (mg/dL) | 48.59 ± 9.4 | 46.81 ± 5.8 | 41.23 ± 3.7 |
| Creatinine (mg/dL) | 2.09 ± 1.3 | 1.56 ± 0.4 | 0.80 ± 0.1 |
| Glucose (mg/dL) | 64.95 ± 2.3 | 77.60 ± 3.0 | 108.42 ± 4.7 |

In animals injected with test compound, cholesterol levels are slightly decreased compared to control group. Further, only at highest concentration of test compound a slight variation of serum creatinine, blood urea nitrogen (BUN) is noticed (Table 4). Taken together, these results suggest that below 25 mg/kg body weight test compound do not cause any significant renal impairment and hepatic damage.

TABLE 4

Effect of test compound on clinical biochemistry patterns relevant to liver and kidney functions.

|  | | IM-1372-Kn-13 (mg/kg body weight) | | | |
| --- | --- | --- | --- | --- | --- |
| Parameters | Control | 50 | 25 | 10 | 5 |
| AST (U/L) | 39 | 128 | 74.5 | 66 | 63 |
| ALT (U/L) | 60 | 95 | 67 | 66 | 48 |
| Creatinine (mg/dL) | 0.4 | 0.9 | 0.35 | 0.4 | 0.4 |
| Glucose (mg/dL) | 85 | 102 | 96 | 100 | 101 |
| BUN (mg/dL) | 21 | 29 | 24.5 | 21 | 18 |
| Cholesterol (mg/dL) | 223 | 178 | 163.5 | 175 | 175 |

Discussion: Experimental screening method is important for ascertaining the safety and efficacy of these synthetic compounds as well as to establish their active components. The acute toxicity study of the drug indicated some changes in the behavior in the animals immediately after injecting the compound and after 1 h all animals became normal. Also no adverse gastrointestinal effects were observed in all the mice used in the experiment. One mouse that received 50 mg/kg of the drug died within 24 h of injection and the histopathology of the mouse showed inflammation in the liver along with infiltration of inflammatory cells particularly lymphocyte noticed in peri-portal region of liver, and in Kidney moderate capsular thickening and fibrosis noticed in the renal capsules. Glomerulus and tubular region appeared normal, while the animals that received 25 mg/kg, 10 mg/kg and 5 mg/kg dose survived beyond the 24 h of observation and there was no inflammation found in liver, kidney and spleen all organs appeared normal. The median acute toxicity value ($LD_{50}$) of the drug was determined to be 25 mg/kg body weight. The viscera of the dead animals did not show any macroscopic changes that could point to the cause of the death. However, since the animals did not convulse before dying, it postulated that the drug did not kill the mice by some action on the nervous system. In the present study, we demonstrate that IM-1372-Kn-13 drug is effective in inhibiting the growth of pancreatic cancer cells in culture as well as in the in vivo model. Our results reveal that IM-1372-Kn-13 treatment drastically reduced the survival of pancreatic cancer (pan02) cells in a dose dependent manner. On the other hand IM-1372-Kn-13 failed to show any cytotoxic effects on the growth of pancreatic cancer (Pan-02) cells at 25 mg/kg concentration. Suppression of pancreatic cancer (Pan-02) cell growth by IM-1372-Kn-13 in our model was due to induction of apoptosis. In summary, this preclinical study using in vitro and in vivo pancreatic cancer models shows that IM-1372-Kn-13 is effective as a monotherapy of pancreatic cancer primarily by inhibition of proliferation and induction of apoptosis. In vitro results revealed that IM-1372-Kn-13 could be successfully used to potentiate induction of apoptosis in the tumor cells.

SIGNIFICANCE OF THE INVENTION

The nimbolide compounds prepared are novel synthetic derivatives, which are useful as anti-cancer agents.

ADVANTAGES OF THE INVENTION

1. The main advantage of the present invention is that it provides novel and useful synthetic nimbolide derivatives.

2. The advantage of the present invention is that it provides an efficient method of preparation for the above nimbolide derivatives.

3. Another advantage of the present invention is the use of these nimbolide derivatives as potential anti-cancer agents.

We claim:

1. A nimbolide analog of formula I and a pharmaceutically acceptable salt thereof:

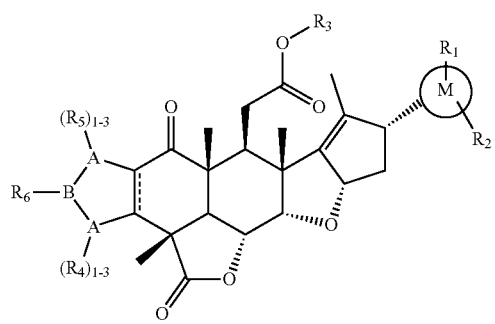

formula I wherein, ring M is a ring selected from the group consisting of substituted or unsubstituted aryl, heteroaryl, cycloalkyl and heterocyclic; and (i) when A and B are each independently selected from the group consisting of C, N, and S, then $R_1$, $R_2$, $R_3$, $R_4$, $R_5$ and $R_6$ are each independently selected from the group consisting of $C_1$-$C_6$ alkyl, aryl, heteroaryl, $C_3$-$C_7$ cycloalkyl, heteroalkyl, hydrogen, hydroxy, alkoxy, nitro, halogen, amino, alkylamino, aryl amino and cyano, wherein each of the $C_1$-$C_6$ alkyl, aryl, heteroaryl, $C_3$-$C_7$ cycloalkyl, heteroalkyl, alkoxy, amino, alkylamino, and aryl amino is optionally substituted with one or more substituents selected from the group consisting of hydroxy, halogen, cyano, alkyl amino, aryl amino, alkoxy, amino, nitro, aldehyde, carboxylic acid and ester;

(ii) when A and/or B is O, then $R_1$, $R_2$, and $R_3$ are each independently selected from the group consisting of $C_1$-$C_6$ alkyl, aryl, heteroaryl, $C_3$-$C_7$ cycloalkyl, heteroalkyl, hydrogen, hydroxy, alkoxy, nitro, halogen, amino, alkylamino, aryl amino and cyano, wherein each of the $C_1$-$C_6$ alkyl, aryl, heteroaryl, $C_3$-$C_7$ cycloalkyl, heteroalkyl, alkoxy, amino, alkylamino, and aryl amino is optionally substituted with one or more substituents selected from the group consisting of hydroxy, halogen, cyano, alkyl amino, aryl amino, alkoxy, amino, nitro, aldehyde, carboxylic acid and ester;

(iii) when A is O, then $R_4$ and $R_5$ are not present; and (iv) when B is O, then $R_6$ is not present; and wherein the dashed bond line in formula I indicates the presence of either a single or double bond.

2. A nimbolide analog selected from the group consisting of

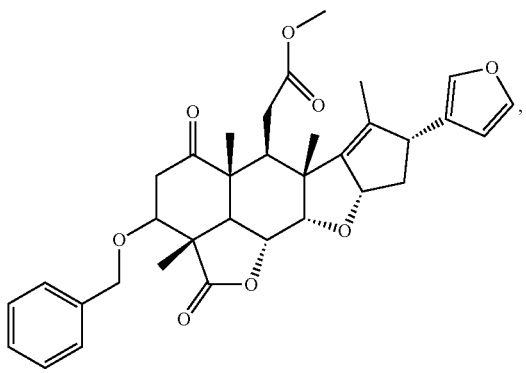

2

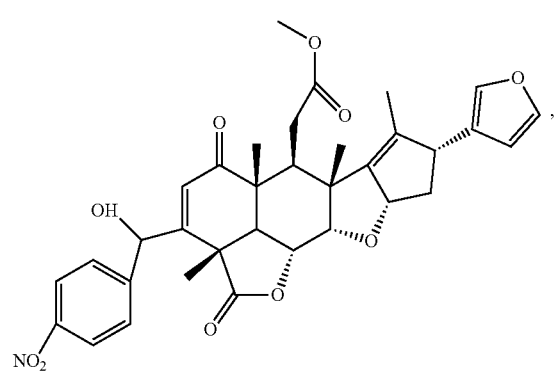

3

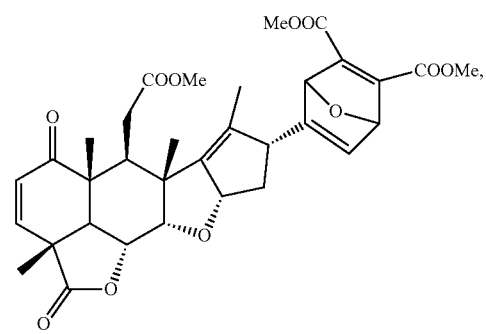

4

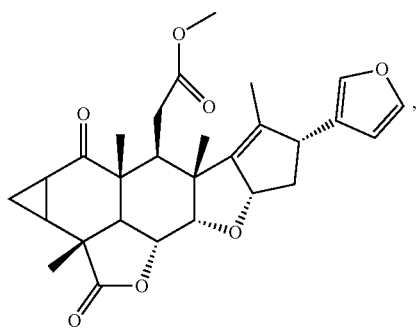

5

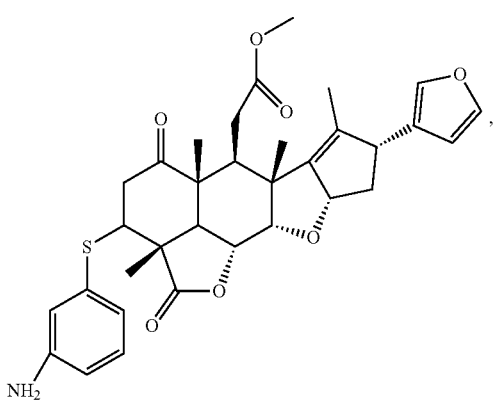

and a pharmaceutically acceptable salt thereof.

3. The nimbolide analog and a pharmaceutically acceptable salt thereof according to claim 1, wherein the pharmaceutically acceptable salt includes a salt of a basic or an acidic group present in compounds of formula I, wherein the basic salt comprises aluminum, calcium, lithium, magnesium, potassium or sodium and the acidic salt comprises hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate or p-toluenesulfonate.

4. A pharmaceutical composition comprising a compound of formula I and a pharmaceutically acceptable salt thereof, and a pharmaceutically acceptable excipient, formula I wherein, ring M is a ring selected from the group consisting of substituted or unsubstituted aryl, heteroaryl, cycloalkyl and heterocyclic; and (i) when A and B are each independently selected from the group consisting of C, N, and S, then $R_1$, $R_2$, $R_3$, $R_4$, $R_5$ and $R_6$ are each independently selected from the group consisting of $C_1$-$C_6$ alkyl, aryl, heteroaryl, $C_3$-$C_7$ cycloalkyl, heteroalkyl, hydrogen, hydroxy, alkoxy, nitro, halogen, amino, alkylamino, aryl amino and cyano, wherein each of each of the $C_1$-$C_6$ alkyl, aryl, heteroaryl, $C_3$-$C_7$ cycloalkyl, heteroalkyl, alkoxy, amino, alkylamino, and aryl amino is optionally further substituted with one or more substituents selected from the group consisting of hydrogen, hydroxy, halogen, cyano, alkyl amino, aryl amino, alkoxy, amino, nitro, aldehyde, carboxylic acid and ester;

(ii) when A and/or B is O, then $R_1$, $R_2$, and $R_3$ are each independently selected from the group consisting of $C_1$-$C_6$ alkyl, aryl, heteroaryl, $C_3$-$C_7$ cycloalkyl, heteroalkyl, hydrogen, hydroxy, alkoxy, nitro, halogen, amino, alkylamino, aryl amino and cyano, wherein each of the $C_1$-$C_6$ alkyl, aryl, heteroaryl, $C_3$-$C_7$ cycloalkyl, heteroalkyl, alkoxy, amino, alkylamino, and aryl amino is optionally further substituted with one or more substituents selected from the group consisting of hydrogen, hydroxy, halogen, cyano, alkyl amino, aryl amino, alkoxy, amino, nitro, aldehyde, carboxylic acid and ester;

(iii) when A is O, then $R_4$ and $R_5$ are not present; and (iv) when B is O, then $R_6$ is not present; and wherein the dashed bond line in formula I indicates the presence of either a single or double bond.

5. The pharmaceutical composition according to claim 4, wherein the pharmaceutically acceptable excipient is selected from the group consisting of sucrose, lactose, xylitol, starch, sorbitol, gelatin, magnesium stearate, carboxymethyl cellulose, mint, cherry, fumed silica, magnesium carbonate, vegetable stearin, steric acid, methyl paraben, propyl paraben, retinyl palmitate, selenium, cysteine, methionine and citric acid.

6. A process for preparing the nimbolide analog according to claim 2, the method comprising the steps of:
   a) treating nimbolide with an organic reagent selected from the group consisting of benzyl alcohol, nitrobenzaldehyde, trihalobenzaldehyde, aminothiophenol, dialkylacetylene dicarboxylate, trialkyllsulfoxonium iodide, sodium borohydride, lithium borohydride, sodium hydride and palladium on carbon, respectively, in an organic solvent and optionally in presence of a base at a temperature in the range of −5 to 150° C. for a period in the range of 1-50 h, and
   b) purifying the product.

7. The process according to claim 6, wherein the base is selected from the group consisting of DBU, imidazole, trimethylamine, pyridine, NaOH, KOH, $NaHCO_3$, $K_2CO_3$, $NH_4Cl$, $Na_2SO_4$ and $NiCl_2.6H_2O$.

8. The process according to claim 6, wherein the organic solvent is selected from the group consisting of ethers, alcohols, toluene, dimethylformamide, dimethylsulfoxide, dioxin, esters, chlorinated organic solvents, hexane, pentane, heptane and acetonitrile.

9. The nimbolide analog and a pharmaceutically acceptable salt thereof according to claim 1, which is useful as an anti-cancer agent.

* * * * *